(12) United States Patent
Swamy et al.

(10) Patent No.: US 11,208,374 B2
(45) Date of Patent: Dec. 28, 2021

(54) N-(7-FLUORO-1,1,3-TRIMETHYL-1 H-INDEN-4YL) AMIDES AND A PROCESS FOR PREPARING SAME

(71) Applicant: FMC Corporation, Philadelphia, PA (US)

(72) Inventors: Narayana Swamy, Bangalore (IN); Chokalingam Devarajan, Bangalore (IN); Ravindra Vitthal Datar, Bangalore (IN)

(73) Assignee: FMC Corporation, Philadelphia, PA (US)

( * ) Notice: Subject to any disclaimer, the term of this patent is extended or adjusted under 35 U.S.C. 154(b) by 60 days.

(21) Appl. No.: 16/665,114

(22) Filed: Oct. 28, 2019

(65) Prior Publication Data

US 2020/0055809 A1  Feb. 20, 2020

Related U.S. Application Data

(62) Division of application No. 16/085,656, filed as application No. PCT/US2017/022441 on Mar. 15, 2017, now Pat. No. 10,570,086.

(60) Provisional application No. 62/309,573, filed on Mar. 17, 2016.

(51) Int. Cl.
| | | |
|---|---|---|
| C07C 209/50 | (2006.01) |
| C07C 211/60 | (2006.01) |
| C07C 231/02 | (2006.01) |
| C07C 231/12 | (2006.01) |
| C07C 209/70 | (2006.01) |
| C07C 233/24 | (2006.01) |
| C07C 233/15 | (2006.01) |
| C07C 209/62 | (2006.01) |
| A01N 37/24 | (2006.01) |
| C07C 233/25 | (2006.01) |

(52) U.S. Cl.
CPC ............ *C07C 209/50* (2013.01); *A01N 37/24* (2013.01); *C07C 209/62* (2013.01); *C07C 209/70* (2013.01); *C07C 211/60* (2013.01); *C07C 231/02* (2013.01); *C07C 231/12* (2013.01); *C07C 233/15* (2013.01); *C07C 233/24* (2013.01); *C07C 233/25* (2013.01); *C07B 2200/07* (2013.01); *C07C 2602/08* (2017.05)

(58) Field of Classification Search
CPC ...... A01N 37/24; C07C 233/15; C07C 233/25
USPC ....................................... 564/222
See application file for complete search history.

(56) References Cited

U.S. PATENT DOCUMENTS

| | | | |
|---|---|---|---|
| 3,681,464 | A | 8/1972 | Theimer |
| 3,936,293 | A | 2/1976 | Rathgeb et al. |
| 4,742,074 | A | 5/1988 | Nishida et al. |
| 5,476,964 | A | 12/1995 | House |
| 9,192,160 | B2 | 11/2015 | Venturini et al. |

FOREIGN PATENT DOCUMENTS

| | | |
|---|---|---|
| CN | 1108239 | 9/1995 |
| CN | 104602523 A | 5/2015 |
| CN | 104995171 A | 10/2015 |
| EP | 0315502 | 5/1989 |
| EP | 0529636 | 3/1993 |
| WO | 20100109301 | 9/2010 |

OTHER PUBLICATIONS

Dahl, et al., "Route Scouting and Process Development of Lu AA26778", Organic Process Research & Development 2008, 12, 429-441.

Oda, et al., J. Pesticide Sci., Structure-Activity Relationships of N-(1,1,3-trimethylindan-4-yl) Carboxamide Fungicides, vol. 18, No. 3, pp. 245-251, 1993.

*Primary Examiner* — Ana Z Muresan
(74) *Attorney, Agent, or Firm* — FMC Corporation

(57) ABSTRACT

The present invention relates to N-(7-fluoro-1,1,3-trimethyl-1H-inden-4yl) amides and a process for preparing same. The novel amides are useful in a process for converting the unwanted S enantiomer form of a 4-aminoindane derivative to its useful raceme.

5 Claims, No Drawings

N-(7-FLUORO-1,1,3-TRIMETHYL -1 H-INDEN-4YL) AMIDES AND A PROCESS FOR PREPARING SAME

CROSS-REFERENCE TO RELATED APPLICATIONS

This application is a Divisional filing of U.S. Ser. No. 16/085,656 that claims the benefit of U.S. Provisional Application No. 62/309,573 the disclosure of which is incorporation herein by reference in its entirety.

TECHNICAL FIELD

The present invention relates to the compound 7-fluoro-1,1,3-trimethyl-2,3-dihydro-1H-inden-4-amine (the "Comp II"), an intermediate useful for the preparation of the fungicidal compound 3-difluoromethyl-N-(7-fluoro-1,1,3-trimethyl-4-indanyl)-1-methyl-4-pyrazolecarboxamide (the "Comp I"). More particularly, the present invention relates to the S enantiomer of Comp II and the preparation thereof. The formulas of Comp I and II are as follows:

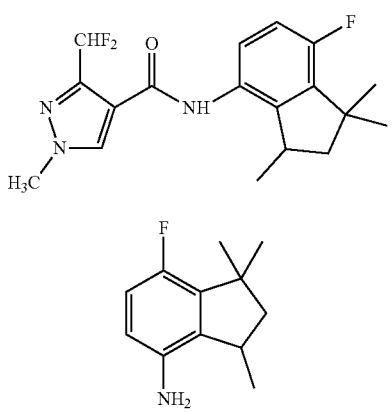

BACKGROUND OF THE INVENTION

The Comp I is a recently discovered fungicidal molecule. The patent application WO2012084812 by Venturini, Isabella et al, first described the Comp I as a fungicide for agricultural use and the synthesis thereof. Structurally, the Comp I is an amide compound and thus can be easily obtained by the routine processes for making those amide compounds. For example, the Comp I can be obtained by condensing the Comp II and a corresponding pyrazole carboxylic acid or pyrazole carboxylic acid halide which provides the corresponding indane portion of the resultant Comp I. The synthesis route is showed as follows:

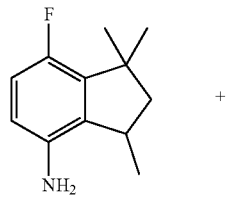

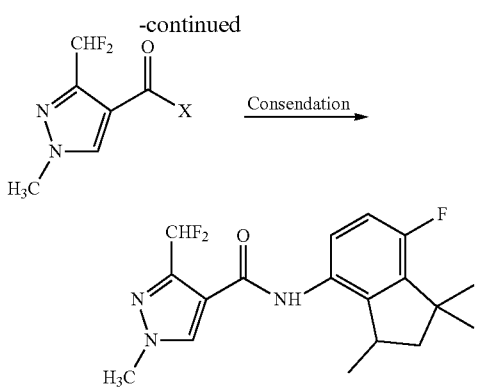

The Comp I is a chiral molecule with a chiral central on the 3'-carbon of the indane ring, which makes the Comp I have two enantiomer forms, namely R and S enantiomers. Further investigation found that the R enantiomer is the active component contributing to the fungicidal activity, while the S enantiomer shows no or less fungicidal activity.

Thus, there is a desire to synthesize in high yield the active component of R enantiomer without the formation of the unwanted inactive S enantiomer. One currently used approach to achieve this goal is using the R enantiomer of Comp II instead of the racemic form thereof as the starting material to react with the corresponding indane derivative to specifically yield the desired R enantiomer. With this approach, the R enantiomer of Comp II is useful while the S enantiomer is useless and wasted.

There is still a strong need to be met where the inactive S enantiomer can be recycled and the active R enantiomer can be synthesized in high yield.

SUMMARY OF THE INVENTION

That need is well fulfilled by the present invention. Thus, in one aspect of the present invention, it provides a novel process for the preparation of (R,S)-7-fluoro-1,1,3-trimethyl-2,3-dihydro-1H-inden-4-amine, starting with (S)-7-fluoro-1,1,3-trimethyl-2,3-dihydro-1H-inden-4-amine, or to say a process for converting (S)-7-fluoro-1,1,3-trimethyl-2,3-dihydro-1H-inden-4-amine to its racemic form, namely (R,S)-7-fluoro-1,1,3-trimethyl-2,3-dihydro-1H-inden-4-amine.

The presently claimed process mainly comprises the steps of:

(a) acylating the (S)-7-fluoro-1,1,3-trimethyl-2,3-dihydro-1H-inden-4-amine to obtain an indaneamide derivative;

(b) oxidizing said indaneamide derivative to obtain 3-hydroxyl indaneamide derivative;

(c) dehydrating said hydroxyl indaneamide derivative to obtain indeneamide derivative;

(d) deacylating said indeneamide derivative to obtain indene amine derivative; and (e) hydrogenating said indene amine derivative to obtain the desired (R,S)-7-fluoro-1,1,3-trimethyl-2,3-dihydro-1H-inden-4-amine.

In another aspect of the present invention, it provides a process fully same to the aforesaid one except that the dehydration step (c) is carried out prior to subsequent to the deacylation step (d), or these two steps are carried out concurrently.

DETAILED DESCRIPTION OF THE INVENTION

The present invention provides a novel process for the preparation of (R,S)-7-fluoro-1,1,3-trimethyl-2,3-dihydro-1H-inden-4-amine ("Formula I"), starting with (S)-7-fluoro-1,1,3-trimethyl-2,3-dihydro-1H-inden-4-amine ("Formula II"). The Formula I and II as well as the entire synthesis route are shown below:

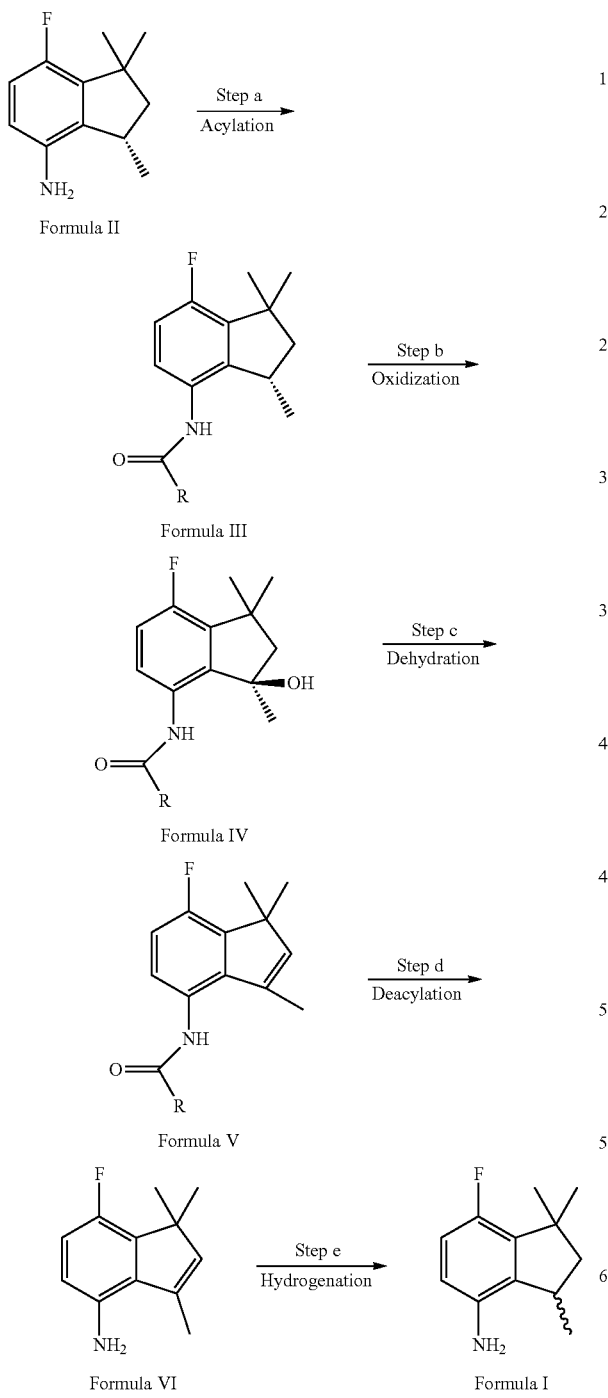

wherein, R is defined as below.

Thus, in one aspect, the present invention provides a process for the preparation of (R,S)-7-fluoro-1,1,3-trimethyl-2,3-dihydro-1H-inden-4-amine, comprising the following steps of:

(a) acylating the (S)-7-fluoro-1,1,3-trimethyl-2,3-dihydro-1H-inden-4-amine to obtain an indaneamide derivative;

(b) oxidizing said indaneamide derivative to obtain hydroxyl indaneamide derivative;

(c) dehydrating said hydroxyl indaneamide derivative to obtain indeneamide derivative;

(d) deacylating said indeneamide derivative to obtain indene amine derivative; and (e) hydrogenating said indene amine derivative to obtain the desired (R,S)-7-fluoro-1,1,3-trimethyl-2,3-dihydro-1H-inden-4-amine.

In another aspect, the present invention provides a process for the preparation of (R,S)-7-fluoro-1,1,3-dihydro-1H-inden-4-amine having the following Formula I, comprising the following steps of:

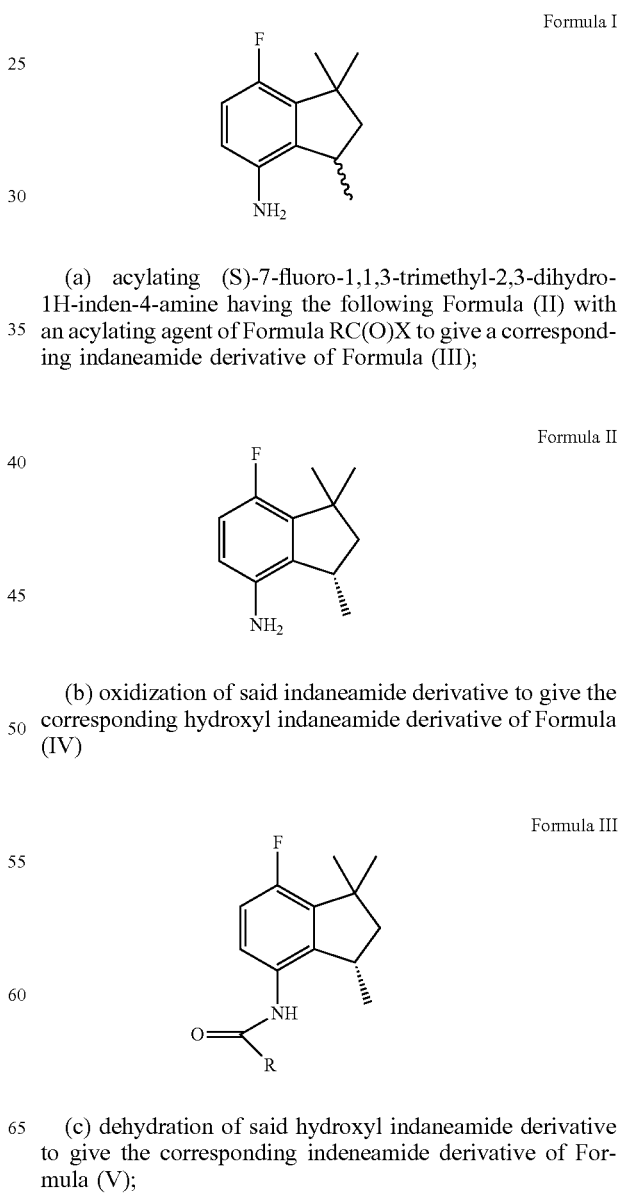

(a) acylating (S)-7-fluoro-1,1,3-trimethyl-2,3-dihydro-1H-inden-4-amine having the following Formula (II) with an acylating agent of Formula RC(O)X to give a corresponding indaneamide derivative of Formula (III);

(b) oxidization of said indaneamide derivative to give the corresponding hydroxyl indaneamide derivative of Formula (IV)

(c) dehydration of said hydroxyl indaneamide derivative to give the corresponding indeneamide derivative of Formula (V);

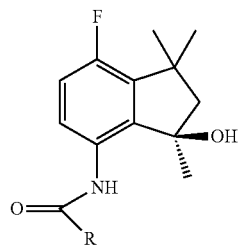

Formula IV (d) deacylation of said indeneamide derivative to give the corresponding indeneamine derivative of Formula (VI); and

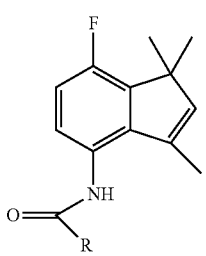

Formula V (e) hydrogenation of said indeneamine derivative to obtain the desired (R,S)-7-fluoro-1,1,3-trimethyl-2,3-dihydro-1H-inden-4-amine,

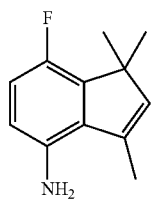

Formula VI wherein,

R is selected from a $C_1$-$C_6$ alkyl group or a $C_6$-$C_{10}$ aryl group, these groups being optionally substituted with one or more of $C_1$-$C_6$ alkyl groups and/or halogen atoms;

X is a leaving group selected from: (i) a hydroxy group; (ii) a halogen atom; (iii) a $C_1$-$C_6$ alkylsulfonyloxy group; (iv) a $C_6$-$C_{10}$ arylsulfonyloxy group, (v) a $R_a$COO group wherein $R_a$ is a $C_1$-$C_6$ alkyl group, the groups (iii)-(v) being optionally substituted with one or more halogen atoms.

Examples of a $C_1$-$C_6$ alkyl group are methyl, ethyl, propyl, butyl, pentyl, hexyl.

Examples of a $C_6$-$C_{10}$ aryl group are phenyl, naphthyl.

Examples of halogen atoms are fluorine, chlorine, bromine, iodine.

The process of the present invention is carried out in the order as indicated above.

In one embodiment of the present processes, the order of the reactions between dehydration step (c) and deacylation step (d) can be changed. In another embodiment, step (c) is carried out prior to or subsequent to step (d). In a further embodiment, step (c) and step (d) are carried out concurrently.

In one embodiment, in step (a) of the present invention, the acylating agent RC(O)X for illustrative purpose is selected from acyl halide and anhydride, preferably acyl halide and anhydride of a lower alkanoic acid, more preferably selected from acetyl chloride, acetic anhydride or mixture thereof. However, one skilled in the art will appreciate that numerous alternative acylating agents can be used interchangeably in step (a) In another embodiment, the step (a) is carried out at elevated temperature, preferably ranging from about 80° C. to about 120° C., more preferably ranging from about 80° C. to about 100° C. In another embodiment, step (a) comprises adding the compound of Formula (II) to freshly distilled acetic anhydride.

In one embodiment, in step (b) of the present invention, the oxidization comprises reacting the indaneamide derivative of Formula (III) in the presence of oxidizing agent to yield the corresponding hydroxyl indaneamide derivative of Formula (IV). In another embodiment, the oxidizing agent for illustrative purpose is selected from the group consisting of $KMnO_4$, $MnO_2$, $SeO_2$, $CrO_3$, or mixture thereof, preferably $KMnO_4$. The skilled one in the art will appreciate numerous alternative oxidizing agent can be used interchangeably in step (b) of the present invention. In another embodiment, the reaction of step (b) is carried out at room temperature under stirring, preferably in the presence of $MgSO_4$.

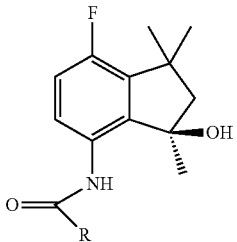

Formula IV

In one embodiment, in step (c) of the present invention, the dehydration comprises reacting said hydroxyl indaneamide derivative of Formula (IV) in the presence of a strong acid to yield indeneamide derivative of formula (V). In another embodiment, the reaction is carried out in an organic solvent, preferably selected from hexane, heptanes, methylene chloride, dichloroethane, methanol, ethanol, isopropanol, toluene, ethyl acetate and mixtures thereof. In another embodiment of step (c), the strong acid is selected from the group consisting of HCl, HBr, $H_2SO_4$ or mixtures thereof, with con. HCl and $H_2SO_4$ more preferred. In another embodiment, the reaction is carried out at room temperature, preferably ranging from about 20° C. to about 40° C., more preferably about 25° C. In another embodiment, the reaction is carried out at elevated temperature under stirring. In another embodiment, the reaction of step (c) is carried out without solvent.

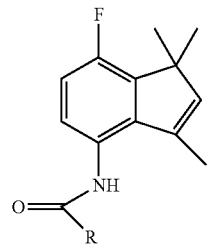

Formula V

In one embodiment, in step (d) of the present processes, the deacylating comprises contacting said indeneamide derivative with a strong add, under elevated temperature to give an addition salt of indeneamine derivative; and then said indeneamine is treated with a base solution, to yield the indeneamine of Formula (VI). In another embodiment, for the illustrative example the strong add is selected from the group consisting of HCl, HBr, $H_2SO_4$ or mixtures thereof, with con. HCl and $H_2SO_4$ more preferred. In another embodiment, the reaction is carried out at the elevated temperature ranging from about 90° C. to about 120° C., preferably ranging from about 100° C. to about 120° C. In another embodiment, the base is selected from NaOH, $NaHCO_3$, KOH and mixtures thereof.

Formula VI

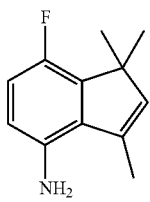

In one embodiment, in step (e) of the present invention, the hydrogenation comprises reacting said indeneamine derivative with gaseous hydrogen in the presence of a hydrogenation catalyst, to obtain the desired (R,S)-7-fluoro-1,1,3-trimethyl-2,3-dihydro-1H-inden-4-amine. In another embodiment, the reaction is carried out in an organic solvent, preferably a polar solvent, more preferably selected from hexane, heptanes, methylene chloride, dichloroethane, methanol, ethanol, isopropanol, toluene, ethyl acetate and mixtures thereof. The illustrative examples of the hydrogenation catalyst include Group (X) metal catalysts, such as nickel, palladium and platinum, preferably Pd—C catalyst. In another embodiment, the reaction of step (e) is carried out without solvent.

Formula I

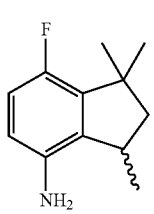

In another aspect of the present invention, it provides a racemate of (R,S)-7-fluoro-1,1,3-trimethyl-2,3-dihydro-1H-inden-4-amine which is prepared according to the present claimed processes.

In a further aspect of the present invention, it provides a compound of Formula V, where the R group is defined as above in the present application. In one embodiment, the present invention provides a compound of N-(7-fluoro-1,1,3-trimethyl-1H-inden-4yl)acetamide.

Formula V

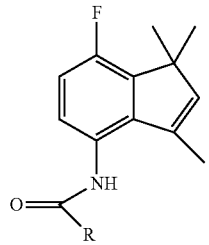

In a further aspect of the present invention, it relates to use of the compound of Formula V for the preparation of (R,S)-7-fluoro-1,1,3-trimethyl-2,3-dihydro-1H-inden-4-amine. In one embodiment, it relates to use of N-(7-fluoro-1,1,3-trimethyl-1H-inden-4yl)acetamide for the preparation of (R,S)-7-fluoro-1,1,3-trimethyl-2,3-dihydro-1H-inden-4-amine.

In a further aspect of the present invention, it relates to a compound of Formula IV where the R group is defined as above in the present application. In one embodiment, the compound of Formula IV is (S)—N-(7-fluoro-1,1,3-trimethyl-3-hydroxy-1H-indan-4-yl)acetamide.

In a yet further aspect of the present invention, it provides a compound of Formula VI, 7-fluoro-1,1,3-trimethyl-1H-inden-4-amine.

The advantages of the presently claimed invention as described above are apparent to the skilled one in the art. With the processes of the present invention, the unwanted (S)-7-fluoro-1,1,3-trimethyl-2,3-dihydro-1H-inden-4-amine can be converted back to its raceme form and further recycled to produce the desired active form of R enantiomer. Therefore, the present process is more environmentally friendly and more cost effective which was never reported or envisioned before.

The following examples are provided for illustrative purpose, and shall not be construed in any way to restrict the scope of the presently claimed invention.

EXAMPLES

Example 1

Step (a)—Acylation: Preparation of (S)—N-(7-fluoro-1,1,3-trimethyl-2,3-dihydro-1H-inden-4-yl) acetamide of Formula (III)

(S)-7-fluoro-1,1,3-trimethyl-2,3-dihydro-1H-inden-4-amine (6 g, 31 mmol) was added to freshly distilled acetic anhydride (4 mL) and stirred at 90° C. for 30 min. Upon completion, reaction mixture was cooled to room temperature and was quenched by water (20 ml). The reaction mixture was extracted with ethyl acetate (50 mL). The organic layer was dried over Na2SO4 and concentrated in vacuo to leave a crude solid of (S)—N-(7-fluoro-1,1,3-trimethyl-2,3-dihydro-1H-inden-4-yl)acetamide (7.1 g) that was analyzed by GC: 97.5%.

Step (b)—Oxidization: Preparation of (S)—N-(7-fluoro-1,1,3-trimethyl-3-hydroxy-1H-indan-4-yl) acetamide of Formula (IV)

15% MgSO4 solution was prepared (4.6 g, 38 mmol). To this solution (S)—N-(7-fluoro-1,1,3-trimethyl-2,3-dihydro-1H-inden-4-yl)acetamide (6 g, 25.5 mmol) obtained from Step (a) dissolved in acetone (90 mL) was added at room temperature. To this solution KMnO$_4$ (9.26 g, 58.6 mmol) in solid form was added in portions and stirred at room temperature for 5 hours. Upon completion, reaction mixture was quenched by 1N NaOH solution to basic pH. The reaction mixture was extracted with ethyl acetate (50 mL). The organic layer was dried over Na$_2$SO$_4$ and concentrated in vacuo to leave a crude solid of (S)—N-(7-fluoro-1,1,3-trimethyl-3-hydroxy-1H-indan-4-yl)acetamide (5.1 g) that was analyzed by GC: 83.5% A.

Step (c)—Dehydration: Preparation of N-(7-fluoro-1,1,3-trimethyl-1H-inden-4yl)acetamide of Formula (V)

Methanol (30 mL) was added to (S)—N-(7-fluoro-1,1,3-trimethyl-3-hydroxy-1H-indan-4-yl)acetamide obtained from Step (b) (5 g, 19.8 mmol). To this solution conc. HCl (10 mL) was added at room temperature and stirred for 90 min. The reaction mixture was diluted with water (100 mL) and extracted with ethyl acetate (50 mL). The organic layer was dried over Na$_2$SO$_4$ and concentrated in vacuo to leave a crude solid of N-(7-fluoro-1,1,3-trimethyl-1H-inden-4yl) acetamide (4 g) that was analyzed by GC: 90.8% A.

Step d—Deacetylation: Preparation of 7-fluoro-1,1,3-trimethyl-1H-inden-4-amine of Formula (VI)

25 g of 50% H$_2$SO$_4$ was added to N-(7-fluoro-1,1,3-trimethyl-1H-inden-4yl)acetamide obtained from Step (c) (4 g, 17.2 mmol) at room temperature. The reaction mixture was stirred at 115° C. for 5 h. The reaction mixture was then diluted to 25% by adding water. Resulted solids were filtered, washed with water and then with hexane. The resulted solids were added to water (20 mL), basified with 10% NaOH solution (15 mL) and stirred at room temperature for 1 h. The reaction mixture extracted with ethyl acetate (20 mL). The organic layer was dried over Na$_2$SO$_4$ and concentrated in vacuo to leave a crude solid of 7-fluoro-1,1,3-trimethyl-1H-inden-4-amine (2.2 g) that was analyzed by GC: 95.5% A.

Step e—Hydrogenation: Preparation of (R,S)-7-fluoro-1,1,3-trimethyl-2,3-dihydro-1H-inden-4-amine of Formula (I)

Methanol (20 mL) was added to 7-fluoro-1,1,3-trimethyl-1H-inden-4-amine obtained from Step (d) (1 g, 7.6 mmol). To this solution 10% Pd—C (50 mg, 0.05 mmol) was added at room temperature. Dry hydrogen gas was bubbled through gas bubbler at room temperature under stirring for 2 h. The reaction mixture was filtered and concentrated in vacuo to leave a crude solid (0.9 g) that was analyzed by GC: 83% A. It was further purified through crystallization by dissolving in hexane (7 mL) at 50° C. and allowed to stand at room temperature for 5 h. The resulted solids were filtered and dried in vacuo and the obtained solids of (R,S)-7-fluoro-1,1,3-trimethyl-2,3-dihydro-1H-inden-4-amine (225 mg) was analyzed by GC: 95% A. The racemic mixture was determined by chiral HPLC: 47:53 (R:S) and by specific rotation [α]D25 −1.45, C=0.15% in methanol.

The invention claimed is:
1. A compound of Formula V,

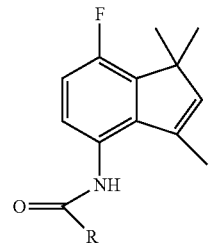

Formula V wherein, R is: (i) C$_1$-C$_6$ alkyl group or (ii) a C$_6$-C$_{10}$ aryl group, wherein group (i) or group (ii) is optionally substituted with one or more of C$_1$-C$_6$ alkyl groups and/or halogen atoms.

2. The compound of claim 1, which is N-(7-fluoro-1,1,3-trimethyl 1H-inden-4yl)acetamide.

3. The compound of claim 1 prepared by a process starting from Formula (II), which is (S)-7-fluoro-1,1,3-trimethyl-2,3-dihydro-1H-inden-4-amine,

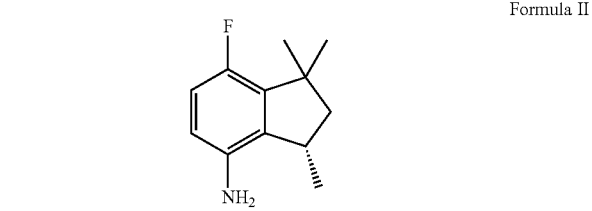

Formula II and the process comprising the steps of:
(a) acylating the (S)-7-fluoro-1,1,3-trimethyl-2,3-dihydro-1H-inden-4-amine to obtain an indaneamide derivative;
(b) oxidizing said indaneamide derivative to obtain 3-hydroxyl indaneamide derivative;
(c) dehydrating said 3-hydroxyl indaneamide derivative to obtain the compound of Formula V.

4. The compound of claim 3 which is N-(7-fluoro-1,1,3-trimethyl-1H-inden-4yl)acetamide.

5. A compound of Formula V,

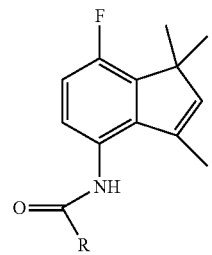

Formula V wherein, R is: (i) a C$_1$-C$_6$ alkyl selected from the group consisting of methyl, ethyl, propyl, butyl, pentyl and hexyl; or (ii) a C$_6$-C$_{10}$ aryl group selected from the group consisting of phenyl and napthyl groups, wherein group (i) or group (ii) is optionally substituted with one or more of C$_1$-C$_6$ alkyl groups and/or halogen atoms.

* * * * *